United States Patent [19]

Warriner

[11] Plant 4,461

[45] Sep. 25, 1979

[54] ROSE PLANT

[75] Inventor: William A. Warriner, Tustin, Calif.

[73] Assignee: Jackson & Perkins Company, Medford, Oreg.

[21] Appl. No.: 951,298

[22] Filed: Oct. 13, 1978

[51] Int. Cl.[2] ..... A01H 5/00

[52] U.S. Cl. ..... Plt./11

[58] Field of Search ..... Plt./11

*Primary Examiner*—Robert E. Bagwill

*Attorney, Agent, or Firm*—Klarquist, Sparkman, Campbell, Leigh, Hall & Whinston

[57] ABSTRACT

An upright, branching rose plant of the hybrid tea class, having large leathery foliage, possessing strong photochemical reaction in the pigment of the flower, with a complex blend of flower color and a slight fragrance.

10 Drawing Figures

BACKGROUND OF THE INVENTION

The present invention relates to a new and distinct variety of rose plant of the hybrid tea class which was originated by me by crossing an unnamed variety with pollen of the variety Spellbinder, U.S. Plant Pat. No. 3,571. This new variety has the same parent varieties and is a sibling from the same seed lot as the variety Color Magic, U.S. Plant Pat. No. 3,998. It differs from Color Magic in many ways as will be seen in the accompanying illustration and description.

The primary objective of this breeding was to produce a new rose variety of the hybrid tea class, possessing the strong photochemical reaction in the pigment of the flower of the pollen parent, but having different plant characteristics, flower form and flower color. This objective was substantially achieved as evidenced by the following unique combination of characteristics, which are outstanding in the new variety and which distinguish it from its parent and siblings as well as from all other varieties of which I am aware:

1. A very vigorous upright habit of growth.
2. Large, leathery foliage similar to that of Spellbinder and Color Magic.
3. Petalage of 40 to 50 petals.
4. Opening flower form sometimes divided into sections or "quartered."
5. A complex blend of flower colors, ranging from Majolica Yellow to Signal Red to Dawn Pink, as noted in the detailed description.
6. A slight fragrance.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:

*Seed parent.*—Unnamed variety.

*Pollen parent.*—Spellbinder.

Classification:

*Botanical.*—Rosa hybrid.

*Commercial.*—Hybrid tea.

FLOWER

Observations made from specimens grown at Irvine, Calif., in July of 1978.

Blooming Habit: Continuous.

Bud:

*Size.*—1 to 1¼ inches when petals start to unfurl.

*Form.*—Rather short, occasionally quartered.

*Color.*—When sepals first divide, mottled colors, mostly Claret Rose (021/1) and (021/2) with some mottling near or lighter than (021/3); area immediately beneath petals mostly near Majolica Yellow (09/2); when half blown, upper side of petals near Dawn Pink (523) until exposed to sunlight, then darkening to Signal Red (719/3). Blended near base with Majolica Yellow (09/2) to Indian Yellow (6) at point of attachment; lower side of petals near Signal Red (719/3) mottled with Dawn Pink (523) near tips, blended with Majolica Yellow (09/1) at center of petal; the Majolica Yellow (09/1) being the most predominant color on the lower side of the petals at the half blown stage.

*Sepals.*—Color: outer surface Scheele's Green (860/3) overlaid in irregular areas with a color lighter, but similar to Garnet Brown (00918/3); inner surface: Scheele's Green (860/3) with a very light tomentum. Three appendaged sepals, lightly appendaged. Two unappendaged sepals, hairy edged.

*Receptacle.*—Color: Scheele's Green (860/3) overlaid irregularly with Garnet Brown (00918/3). Shape: funnel. Size: large, broad, long. Surface: smooth and glaucescent.

*Peduncle.*—Length: short. Surface: smooth, has few very small prickles. Color: light green, bronzy. Strength: stiff, heavy erect.

*Opening.*—With very little recurving of petals, often showing "quartering" in center.

BLOOM

Size: Large, average open size 4"–5".

Borne: Mostly singly.

Stems: Long, strong.

Form: When first open, high centered. Permanence — flattens.

Petalage: Number of petals under normal conditions, 45–50.

Color: Center of flower: upper side of petals, blend of Majolica Yellow (09/2) and Dawn Pink (523) to large area of Indian Yellow (6) becoming more intense at point of attachment. Reverse side of petals, less yellow, shows more Dawn Pink (523) blending with yellow which becomes clear Indian Yellow (6) at point of attachment. Base of petals: mostly Indian Yellow (6); outer petals: when newly opened become mostly Geranium Lake (20/1 to 20/2), some less exposed areas are lighter, Geranium Lake (20/3). General tonality from a distance: Geranium Lake (20/1) and Majolica Yellow (09/2) near center.

Variegation discoloration third day: more petals become Geranium Lake (20/1) until after several days the color is all Geranium Lake (20/1).

Fragrance: Slight.

Petals:

*Texture.*—Thick, leathery.

*Shape.*—Obovate

*Form.*—Flat, and sometimes creased at center midrib.

*Arrangement.*—Irregular. Petaloids in center, few.

*Persistence.*—Drop off cleanly.

*Lastingness.*—On the plant, long; as cut flower, long.

Reproductive parts:

*Anthers.*—Large. Color — yellow. Arrangement, regular around styles.

*Filaments.*—Color: Mars Orange (013).

*Pollen.*—Gold Yellow.

*Styles.*—Color: Oxblood Red (00823/3).

*Stigmas.*—Color: yellow.

PLANT

Form: Bush.

Growth: Very vigorous, upright, branching.

Foliage: Number of leaflets on normal midstem leaves, usually 5.

Size: Large.

Quantity: Normal.

Color: New foliage: Garnet Brown (00918/3) Old foliage: near Spinach Green (0960).

Leaflets:

*Shape.*—Elliptic.

*Texture.*—Upper side — leathery, slightly corrugated.

*Edge.*—Serrated.

*Serration.*—Single, small.

*Petiole.*—Rachis: Color, green below, reddish above. Underside, prickles. Upper edges have a few stipitate glands.

*Stipules.*—Long, bearded.

*Desease resistance.*—Normally resistant to mildew under normal growing conditions at Irvine, Calif.

Wood:

*New Wood.*—Color: bronzy brown. Bark: smooth.

*Old Wood.*—Color: green to brown. Bark: relatively smooth.

Prickles:

*Quantity.*—On main stalks from base, ordinary. On laterals from stalk, ordinary.

*Form.*—Very long base, hooked downward.

*Color when young.*—Red.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its upright, branching plant, its large leathery foliage, its 40 to 50 petals, sometimes quartered flower form, its complex blend of flower color from Majolica Yellow to Signal Red to Dawn Pink and its slight fragrance.

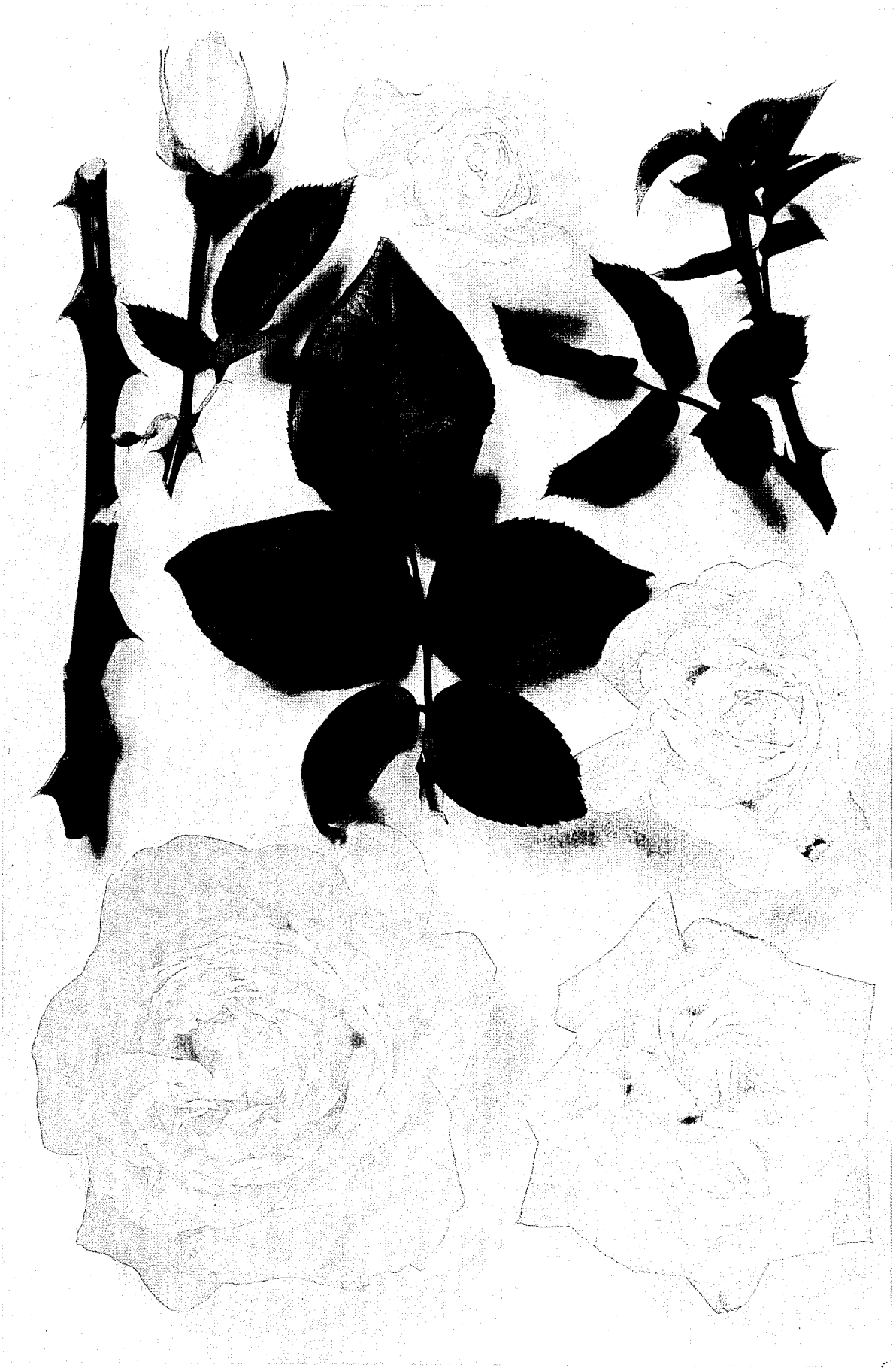

* * * * *